US012793857B2

(12) United States Patent
Awasthi

(10) Patent No.: US 12,793,857 B2
(45) Date of Patent: Nov. 10, 2026

(54) APPARATUS AND METHOD FOR DETERMINING A PATIENT SURVIVAL PROFILE USING ARTIFICIAL INTELLIGENCE-ENABLED ELECTROCARDIOGRAM (ECG)

(71) Applicant: Anumana, Inc., Cambridge, MA (US)

(72) Inventor: Samir Awasthi, Jamaica Plain, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/229,854

(22) Filed: Aug. 3, 2023

(65) Prior Publication Data

US 2025/0046461 A1 Feb. 6, 2025

(51) Int. Cl.
*G16H 50/30* (2018.01)
*A61B 5/00* (2006.01)
(Continued)

(52) U.S. Cl.
CPC ............. *G16H 50/30* (2018.01); *A61B 5/346* (2021.01); *A61B 5/7267* (2013.01); *A61B 5/7435* (2013.01); *G16H 10/60* (2018.01)

(58) Field of Classification Search
CPC ..... A61B 5/346; A61B 5/7267; A61B 5/7435; G16H 10/60; G16H 50/30
See application file for complete search history.

(56) References Cited

U.S. PATENT DOCUMENTS 6,424,860 B1 * 7/2002 Karlsson .................. A61B 5/35 600/512
9,295,429 B2 3/2016 Ong et al.
(Continued)

OTHER PUBLICATIONS

Groot, A. et al. Measurement of ECG abnormalities and cardiovascular risk classification: a cohort study of primary care patients in the Netherlands. Br J Gen Pract. Jan. 2015;65(630):e1-8. doi: 10.3399/bjgp15X683089. PMID: 25548311; PMCID: PMC4276002. (Year: 2015).*
(Continued)

*Primary Examiner* — Niketa Patel
*Assistant Examiner* — Shreya Anjaria
(74) *Attorney, Agent, or Firm* — CALDWELL LLC

(57) ABSTRACT

An apparatus for determining a patient survival profile using artificial intelligence-enabled electrocardiogram (ECG), the apparatus includes a processor and a memory containing instructions configuring the processor to receive a plurality of patient profiles, wherein each patient profile includes ECG data, define a plurality of cohort labels, wherein defining the plurality of cohort labels includes generating a condition score for each patient profile of the plurality of patient profiles and defining the plurality of cohort labels as a function of the condition score, assign the plurality of cohort labels to the plurality of patient profiles, generate condition training data by correlating the plurality of patient profiles with a plurality of condition identifiers, generate a condition evaluation model and a machine-learning algorithm using the condition training data, determine a patient survival profile for a user-inputted patient profile using the condition evaluation model, and display the patient survival profile at a display device.

16 Claims, 7 Drawing Sheets

(51) Int. Cl.

| | |
|---|---|
| ***A61B 5/346*** | (2021.01) |
| ***G16H 10/60*** | (2018.01) |

(56) References Cited

U.S. PATENT DOCUMENTS

| | | | | |
|---|---|---|---|---|
| 2010/0030302 | A1* | 2/2010 | Blowers | G16H 40/67 705/2 |
| 2015/0282726 | A1* | 10/2015 | Grube | A61B 5/349 600/523 |
| 2016/0035112 | A1* | 2/2016 | Lou | G06T 11/005 382/131 |
| 2018/0032691 | A1* | 2/2018 | Zur | A61B 5/259 |
| 2020/0303072 | A1* | 9/2020 | Drokin | G16H 10/60 |
| 2020/0397313 | A1* | 12/2020 | Attia | A61B 5/316 |
| 2021/0315473 | A1 | 10/2021 | Chan | |
| 2021/0353203 | A1* | 11/2021 | Burman | G16H 50/30 |
| 2022/0047201 | A1* | 2/2022 | Attia | G06N 3/045 |
| 2022/0138510 | A1* | 5/2022 | Dai | G06F 18/24133 706/15 |
| 2022/0249031 | A1 | 8/2022 | Clifton | |
| 2022/0265219 | A1* | 8/2022 | An | G16H 50/30 |
| 2022/0384044 | A1 | 12/2022 | Ulloa-Cerna | |
| 2023/0089991 | A1 | 3/2023 | Attia et al. | |

OTHER PUBLICATIONS

X. Wang, "Interpolation and Sharpening for Image Upsampling," 2022 2nd International Conference on Computer Graphics, Image and Virtualization (ICCGIV), Chongqing, China, 2022, pp. 73-77, doi: 10.1109/ICCGIV57403.2022.00020 (Year: 2022).*

European Search Report; EP24190429.1; Date: Dec. 17, 2024; Bankwitz, Robert.

European Search Report; EP24190429; Date: Dec. 17, 2024.

* cited by examiner

APPARATUS AND METHOD FOR DETERMINING A PATIENT SURVIVAL PROFILE USING ARTIFICIAL INTELLIGENCE-ENABLED ELECTROCARDIOGRAM (ECG)

FIELD OF THE INVENTION

The present invention generally relates to the field of artificial intelligence. In particular, the present invention is directed to an apparatus and method for determining a patient survival profile using artificial intelligence-enabled electrocardiogram (ECG).

BACKGROUND

Chronic diseases represent a significant global health burden, being the leading cause of morbidity and mortality worldwide. This includes conditions such as heart disease, cancer, diabetes, and lung disease. Risk estimation tools have been developed for these chronic conditions to aid in risk stratification and primary prevention. However, existing tools still face challenges in terms of their accuracy and predictive capabilities.

SUMMARY OF THE DISCLOSURE

In an aspect, an apparatus for determining a patient survival profile using artificial intelligence-enabled electrocardiogram (ECG) is described. The apparatus includes at least a processor and a memory communicatively connected to the at least a processor contains instructions configuring the at least a processor to receive a plurality of patient profiles, wherein each patient profile of the plurality of patient profiles includes ECG data, define a plurality of cohort labels, wherein defining the plurality of cohort labels includes generating a condition score for each patient profile of the plurality of patient profiles and defining the plurality of cohort labels as a function of the condition score, assign the plurality of cohort labels to the plurality of patient profiles, generate condition training data by correlating the plurality of patient profiles with a plurality of condition identifiers, generate a condition evaluation model using the condition training data and at least one machine-learning algorithm, determine a patient survival profile for a user-inputted patient profile using the condition evaluation model, and displaying the patient survival profile at a display device.

In another aspect, a method for determining a patient survival profile using artificial intelligence-enabled electrocardiogram (ECG) is described. The method includes receiving, by a processor, a plurality of patient profiles, wherein each patient profile of the plurality of patient profiles includes ECG data, defining, by the processor, a plurality of cohort labels, wherein defining the plurality of cohort labels includes generating a condition score for each patient profile of the plurality of patient profiles and defining the plurality of cohort labels as a function of the condition score, assigning, by the processor, the plurality of cohort labels to the plurality of patient profiles, generating, by the processor, condition training data by correlating the plurality of patient profiles with a plurality of condition identifiers, generating, by the processor, a condition evaluation model using the condition training data and at least a machine-learning model, determining, by the processor, a patient survival profile for a user-inputted patient profile using the condition evaluation model, and displaying the patient survival profile at a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining a patient survival profile using artificial intelligence-enabled electrocardiogram (ECG). In an embodiment, apparatus may use deep electronic health record data (EHR) to create an independent AI/machine learning (ML) model using a plurality of separate neural networks including subjects without known history of ASCVD, to identify coronary artery calcium score by computed tomography, obstructive CAD by stress test, angiography, or procedural intervention, and regional akinesis using echocardiogram, as a reflection of possible prior myocardial infarction (MI). These were ensembled and used to assess the utility of AI/ML model MI risk stratification in a retrospective observational study consisting of patients with PCE scores and no prior ASCVD. Exemplary embodiments illustrating aspects of the present disclosure are described below in the context of several specific examples.

Figure 1:
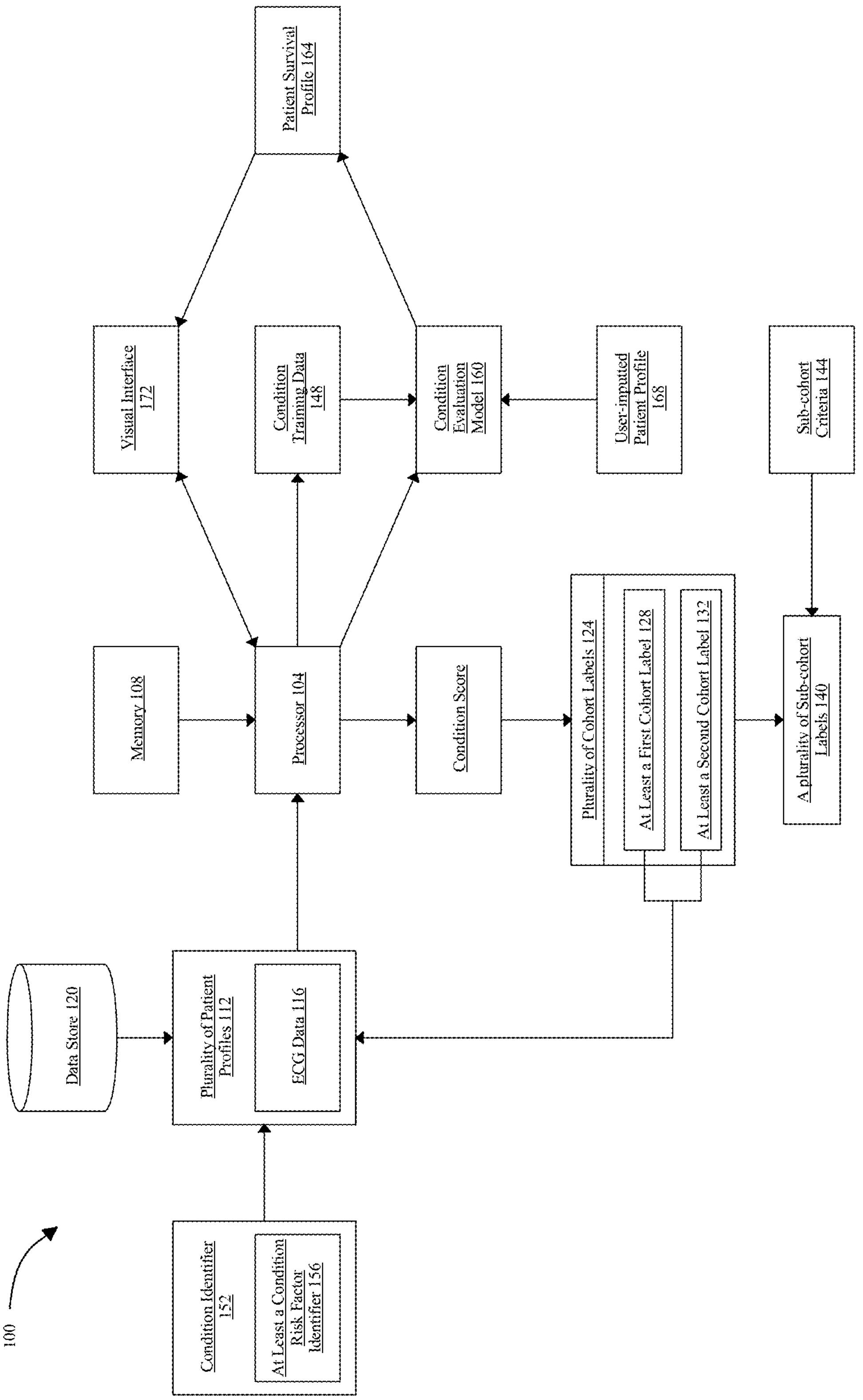
FIG. 1 is a block diagram of an exemplary embodiment of an apparatus for determining a patient survival profile using artificial intelligence-enabled electrocardiogram (ECG)

Referring now to FIG. 1, an exemplary embodiment of an apparatus 100 for determining a patient survival profile using artificial intelligence-enabled electrocardiogram (ECG) is illustrated. System includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of system 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. Memory 108 may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may perform determinations, classification, and/or analysis steps, methods, processes, or the like for the purposes of this disclosure using machine-learning processes. A "machine-learning process," as used in this disclosure, is a process that automatedly uses a body of data known as "training data" and/or a "training set" (described further below in this disclosure) to generate an algorithm that will be performed by processor 104 to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, processor 104 is configured to receive a plurality of patient profiles 112. As used in this disclosure, each "patient profile" of plurality of patient profiles 112 is a comprehensive collection of information related to an individual patient. In some cases, each patient profile of plurality of patient profiles 112 may include a variety of different types of data that, when combined, provide a detailed picture of a patient's overall health. In an embodiment, each patient profile may include demographic data of patient, for example, and without limitation, each patient profile of plurality of patient profiles 112 may include basic information about the patient such as name, age, gender, ethnicity, socioeconomic status, and/or the like. In another embodiment, each patient profile may also include a patient's medical history, for example, and without limitation, each patient profile of plurality of patient profiles 112 may include a detailed record of the patient's past health conditions, medical procedures, hospitalizations, and illnesses such as surgeries, treatments, medications, and/or the like. In another embodiment, each patient profile may include lifestyle Information of patient, for example, and without limitation, each patient profile of plurality of patient profiles 112 may include details about the patient's diet, exercise habits, smoking and alcohol consumption, and other behaviors that could impact health. In a further embodiment, each patient profile may include patient's family history, for example, and without limitation, each patient profile of plurality of patient profiles 112 may include a record of hereditary diseases. As an ordinary person skilled in the art, upon reviewing the entirety of this disclosure, will be aware of various type of data within patient profiles apparatus 100 may receive and process in consistent with this disclosure.

In one or more embodiments, and still referring to FIG. 1, each patient profile of the plurality of patient profiles 112 described herein includes electrocardiogram (ECG) data 116. As used in this disclosure, "electrocardiogram (ECG) data" refers to data related to an electrocardiogram of the patient that corresponds to the patient profile, wherein the "electrocardiogram" is a medical test that records the electrical activity of patient's heart over a period of time. In an embodiment, ECG data 116 may include one or more recordings captured by a plurality of electrodes placed on patient's skin. In some cases, ECG data 116 may include information regarding a P wave, wherein the P wave represents the electrical impulse traveling from the sinoatrial (SA) node through the atria, causing them to contract (atrial depolarization). For example, and without limitation, ECG data 116 of a healthy person may include data describing a normal P wave (i.e., P wave that is positive [above the baseline]), as well as its time duration (e.g., typically less than or equal to 0.11 seconds). In some cases, ECG data 116 may also include, without limitation, T wave (i.e., the ventricular repolarization [the recovery phase for the ventricles]), QRS complex (i.e., rapid depolarization of the right and left ventricles), PR interval (i.e., the time from the onset of the P wave to the start of the QRS complex, representing the time it takes for the electrical signal to travel from the sinus node through the AV node, where it enters the ventricles), ST segment (i.e., The period from the end of the QRS complex to the beginning of the T wave, representing the period when the ventricles are depolarized) the and/or the like. In some cases, ECG data 116 may be acquired at a sampling rate of 250 Hz or 400 Hz using a GE-Marquette ECG machine (Marquette, WI, USA) with raw data stored using the MUSE data management system. Both 250 Hz and 400 Hz are unified into a 400 Hz format.

In a non-limiting example, and still referring to FIG. 1, one or more patient profile of plurality of patient profiles 112 may include ECG data 116 describing normal ECGs, wherein the normal ECGs may indicate normal heart rate (60-100 bpm), regular rhythm, normal P waves preceding each QRS complex, PR interval between 0.12 to 0.20 seconds, QRS duration less than 0.12 seconds, and ST segment and T waves that are appropriate and consistent. In another non-limiting example, one or more patient profiles of plurality of patient profiles 112 may include ECG data 116 describing atrial fibrillations (AF), wherein AF is characterized by irregularly irregular rhythm, absence of P waves, and a variable ventricular response. In this case, ECG data 116 may show a disorganized and irregular rhythm with no discernable P waves. In a further non-limiting example, one or more patient profiles of plurality of patient profiles 112 may include ECG data 116 describing myocardial infarction (MI). Such ECG data 116 of a patient experiencing an MI might show ST elevation (STEMI) or deep Q waves in specific leads depending on the region of the heart muscle experiencing the lack of oxygen.

With continued reference to FIG. 1, in some cases, ECG data 116 may include an ECG interpretation text. "ECG interpretation text," for the purpose of this disclosure, refers to a summary or analysis of the findings from ECG described herein. In some cases, the ECG interpretation text may be in various formats; for example, without limitation, ECG interpretation text may be in not only text format (i.e., a physical written report) but also in other formats such as image, audio, video, or any electronic file. In some cases, ECT interpretation text may be provided by a trained medical professional; for instance, and without limitation, a cardiologist or other healthcare provider who is experienced in reading and interpreting ECGs may provide ECG interpretation text described herein. In an embodiment, ECG interpretation text may translate a graphical data from ECG into a clinically meaningful narrative that can be used to make diagnoses, guide treatment decisions, and track the progression of cardiovascular diseases. In some cases, ECG interpretation text may include any ECG data 116 described herein such as, without limitation, rate and rhythm, axis (i.e., describes an overall direction of the heart's electrical activity and can give insight into different pathologies), Intervals (e.g., PR interval, QRS duration, and QT interval), ST segments and P/T-Waves, and any abnormalities detected. Additionally, or alternatively, ECG interpretation text may describe any significant findings regarding ECG data 116, such as, without limitation, signs of ischemia (lack of oxygen supply to the heart), injury, infarction (heart attack), hypertrophy (enlarged heart), or any other specific ECG changes. In a non-limiting example, ECG interpretation text incorporated by ECG data 116 of a given patient profile may include a text string such as "Sinus rhythm with a rate of 72 bpm. Normal axis. No signs of hypertrophy or chamber enlargement. No significant ST-segment or T wave changes. No Q waves suggestive of infarction. The ECG is normal."

Still referring to FIG. 1, in some cases, ECG interpretation text may include an ECG report, wherein the ECG report may include (a summary of) any specific diagnoses or clinical concerns based on corresponding ECG data 116 described herein. In some cases, ECG interpretation text may also include other data from one or more patient profiles; for instance, and without limitation, ECG interpretation text may include patient information as described above, such as patient's name, age, recent activities, family histories, diet, and/or the like. In a non-limiting example, a first patient may have a patient profile including ECG data containing an ECG interpretation text such as "First Patient: A 30-year-old female, smoker, with no family history of heart disease. ECG data is normal, but she has slightly elevated blood pressure. Her medical history is unremarkable," while a second patient may have another patient profile including ECG data containing another ECG interpretation text such as "Second Patient, 45-year-old male, non-smoker, with a family history of heart disease. His ECG data shows irregular heart rhythms, and he has high cholesterol levels. His medical history reveals a previous heart attack five years ago.

With continued reference to FIG. 1, processor 104 may be configured to receive plurality of patient profile from a data store 120. Data store 120 may be configured to store any data described herein. Processor 104 may be communicatively connected with data store 120. In some cases, data store 120 may be local to processor 104. Alternatively, data store 120 may be remote to processor 104 and communicative with processor 104 by way of one or more networks (e.g., a cloud network, a mesh network, or the like). In a non-limiting example, apparatus 100 may include a "cloud-based" system (i.e., a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network.

Still referring to FIG. 1, in some cases, data store 120 may be implemented, without limitation, as a relational database, a key-value retrieval database such as a NOSQL database, or any other format or structure for use as a database that a person skilled in the art would recognize as suitable upon review of the entirety of this disclosure. Data store 120 may alternatively or additionally be implemented using a distributed data storage protocol and/or data structure, such as a distributed hash table or the like. Data store 120 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a data store or database may store, retrieve, organize, and/or reflect data and/or records as used herein, as well as categories and/or populations of data consistently with this disclosure.

In a non-limiting example, and still referring to FIG. 1, plurality of patient profiles 112 may be retrieved from a deidentified, privacy-preserving database consisting of digital electronic health records (EHR) from 6,938,968 patients seen at over 70 Mayo Clinic hospitals and clinics across Arizona, Florida, Iowa, Minnesota, and Wisconsin, including 3 major health systems, was leveraged for model development and analysis. In some cases, plurality of patient profiles 112 including ECG data 116 may be obtained using an application programing interface (API) of Federated Clinical Analytics Platform (FCAP). In an embodiment, API may convert raw electronic medical record (EMR) data from one or more health systems into an anonymized and semi-structured database such as any database described herein. In a non-limiting example, receiving plurality of patient profiles 112 may include selecting, from the anonymized and semi-structured database, EMR/EHR of all patients ≥18 years old, along with ECG data 116 containing at least one digital 10-second, 12-lead ECG on record.

With continued reference to FIG. 1, processor 104 is configured to define a plurality of cohort labels 124. As used in this disclosure, a plurality of "cohort labels" are classifications or groupings of plurality of patient profiles 112 based on shared characteristics. Plurality of cohort labels 124 may be used by processor 104 to identify one or more patterns within and between groups of similar patients. In some cases, shared characteristics may be a wide range of factors, including but not limited to, demographic data, medical history, genetic data, lifestyle factors, ECG data, and any other data described herein. In a non-limiting example, plurality of cohort labels 124 may be used by processor 104 to categorize plurality of patient profiles 112 and/or patients correspond to plurality of patient profiles 112 into one or more distinct groups for comparative analysis (e.g., prediction of disease progression, treatment outcomes, survival rates, identification of risk factors, and/or the like) as described in greater detail below. In some cases, plurality of cohort labels 124 may include one or more demographic-based labels, wherein the demographic-based labels may be based on demographic characteristics such as, age, gender, ethnicity, and/or any demographic data described herein; for instance, and without limitation, plurality of cohort labels 124 may include "Elderly", "Female", "Hispanic", and so on. In some cases, plurality of cohort labels 124 may include a plurality of disease-based Labels, wherein the plurality of disease-based labels may categorize plurality of patient profiles and/or patients correspond to plurality of patient profiles 112 based on the presence, absence, or risk of certain diseases. Exemplary disease-based labels may include, without limitation, "Diabetic", "Cancer Risk", "Heart Disease", and/or the like.

With continued reference to FIG. 1, in an embodiment, plurality of cohort labels 124 may include at least a first cohort label 128 and at least a second cohort label 132 associated with the at least a first cohort label 128. As used in this disclosure, at least a "first cohort label" and at least a "second cohort label" represent two different groups of patients/patient profiles. In some cases, at least a first cohort label 128 may include a disease cohort; for instance, and without limitation, at least a first cohort label 128 may be assigned to a group of patients who have a specific disease or condition. In some cases, at least a second cohort label 132 may include a control cohort; for instance, and without limitation, at least a second cohort label 132 may be assigned to a group of patients who do not have the specific disease or condition that characterizes the disease cohort described herein. In an embodiment, patient profiles having at least a second cohort label 132 may serve as a control or comparison group for patient profiles having at least a first cohort label 128. For example, and without limitation, if disease cohort consists of patients with heart disease, the control cohort may include patients of similar age, gender, and other demographic characteristics but without heart disease.

Still referring to FIG. 1, defining plurality of cohort labels 124 includes generating a condition score 136 for each patient profile of plurality of patient profiles 112. A "condition score," for the purpose of this disclosure, is a quantified measure that represents the overall health status or severity of a particular disease. In some cases, patient profile may be manually scored by medical professionals described herein. In other cases, condition score 136 may be generated, by processor 104, through one or more scoring algorithm or model such as, without limitation, machine learning models described below, that takes into account various data from each patient profile of plurality of patient profiles 112, including ECG data 116, demographic information, EMR/EHR, lifestyle factors, and other relevant health metrics as described herein. In an embodiment, condition score 136 may then be used to categorize or stratify plurality of patient profiles 112 into different cohorts or groups. In a non-limiting example, depending on the health condition in question, a higher score may indicate a worse prognosis, a higher disease severity, or a higher risk of complications, and vice versa. In some cases, condition score 136 may include a risk score, wherein the risk score may evaluate the risk of developing a particular condition or disease. For example, and without limitation, a cardiovascular risk score may consider factors such as age, gender, cholesterol levels, blood pressure, and smoking status. In some cases, condition score 136 may include a severity score, wherein the severity score may measure the severity or stage of an existing disease or condition. For instance, and without limitation, in the context of heart disease, generating severity score may take into account factors such as the extent of coronary artery blockage, the number of heart attacks a patient has had, and their corresponding ECG data. In other cases, condition score 136 may include a prognostic score, wherein the prognostic score may predict the course or outcome of a disease, such as, without limitation, survival rate or likelihood of recovery. In a non-limiting example, prognostic score may be generated by processor 104 via considering data that describes tumor size, the number of lymph nodes involved, the presence of metastases, the specific type and grade of cancer, and/or the like.

Still referring to FIG. 1, defining plurality of cohort labels 124 includes defining plurality of cohort labels 124 as a function of condition score 136. In a non-limiting example, at least a first cohort label 128 may describe a coronary artery calcification (CAC). Such cohort label may be defined by processor 104, based on a CAC score, wherein the CAC score are measures used to assess the presence and extent of calcification in coronary arteries which supply blood to the heart. In some cases, generating condition score 136 may include extracting condition score 136 from plurality of patient profiles 112 using a plurality of regular expressions. In a non-limiting example, one or more regular expressions will be created to match the specific pieces of information within each patient profile of plurality of patient profiles 112 that are needed by the processor 104 to calculate, generate, or otherwise determine condition score 136. For example, and without limitation, one or more regular expressions may be used to match phrases such as "diabetes diagnosis", "smoking status: current smoker", "blood pressure: 140/90", "BMI: 30", "age: 45", and/or the like. Processor 104 may search through each patient profile of plurality of patient profiles and extract matching data. Once the relevant data has been extracted from each patient profile, processor 104 may calculate, generate, and/or determine condition score 136 as an extracted relevant data.

In a non-limiting example, and still referring to FIG. 1, CAC score may be extracted, directly or indirectly, from each patient profile of plurality of patient profiles 112 using regular expressions described herein from EHRs/EMRs of approximately 33,000 patients that underwent an ECG-gated cardiac CT scan for CAC detection and scoring. In this cases, at least a first cohort label e.g., a disease cohort, may be defined as (adult) patients with a CAC score greater than 200. At least a second cohort label, e.g., a control cohort may be defined as (adult) patients with no coronary artery calcification (i.e., having a CAC score equal to 0), or its synonyms (zero, no, negative, etc.).

Additionally, or alternatively, and still referring to FIG. 1, plurality of cohort labels 124 may be also defined, by processor 104, as a function of a set of pre-defined rules/criteria. In some cases, rules or criteria may be established, by processor 104, based on a variety of factors, such as demographic characteristics, disease status, lifestyle habits, genetic factors, or the condition score described herein. In a non-limiting example, in some cases, at least a first cohort label 128 may describe an obstructive coronary artery disease CAD, wherein such disease cohort may be defined as (adult) patients that met at-least one of the following criteria: 1) Underwent coronary angiography and were found to have severe stenosis and had an ECG on record within 30 days of angiography, with no intervening invasive cardiac procedure or MI, wherein severe stenosis may be defined as: a. ≥50% occlusion of left main coronary artery; and b. ≥70% occlusion, including complete occlusion, of any of the other coronary arteries; 2) Underwent coronary artery bypass graft surgery (CABG) or percutaneous coronary intervention (PCI) without evidence of acute MI or prior MI on record in either structured data (diagnosis codes) or unstructured data (all clinical documents, analyzed using AI-enabled natural language processing14) and had an ECG on record within 90 days preceding CABG/PCI; and 3) Underwent stress echocardiography or nuclear stress testing and were found to be positive for stress-induced myocardial ischemia, and had an ECG on record within 30 days of testing, with no intervening invasive procedure or MI. In this cases, at least a second cohort label, e.g., control cohort may be defined by identifying, using processor 104, (adult) patients without history of CAD in either structured or unstructured data yet enough clinical history present within 2 years of the ECG to calculate 10-year ASCVD risk using the PCE from plurality of patient profiles 112. In some cases, patient profiles having at least a second cohort label 132 may be propensity matched 1:10 to patient profiles having at least a first cohort label 128 based on data such as, without limitation, age, sex, and ECG acquisition year.

In another non-limiting example, and still referring to FIG. 1, at least a first cohort label 128 may include a regional left ventricular akinesis (as possible prior MI), which may be defined, by processor 104, as any (adult) patient with ≥1 left ventricular akinetic segment found during transthoracic echocardiographic assessment of regional wall motion abnormalities, and an ECG on record within 180 days of echocardiography. At least a second cohort label 132 may then be defined as any (adult) patient with zero akinetic, hypokinetic, dyskinetic, or aneurysmal segments, ever, an ECG on record within 180 days of echocardiography, and no history of MI prior to the later of ECG or echocardiography. Additionally, or alternatively, one or more patient profiles within plurality of patient profiles 112 may be excluded, by processor 104, if they contain data indicating left bundle branch block documented in ECG reports or diagnosis codes prior to 30 days post-echocardiography.

Still referring to FIG. 1, in other embodiments, condition score 136 for each patient profile of plurality of patient profiles 112 may be generated as a function of a machine-learning process. In a non-limiting example, processor 104 may generate a condition score machine learning model trained using condition score training data, wherein the condition score training data may include a plurality of patient profiles as input correlate to a plurality of condition score as output. In an embodiment, condition score training data may be received, by processor 104 from data store 120. In another embodiment, condition score training data may include historical patient profiles such as previous ECGs, physical examination result, medical record, and/or the like. Processor 104 may train condition score machine learning model using the condition score training data and generate condition score 136 for each patient profile of plurality of patient profiles 112 using the trained condition score machine learning model. In some cases, condition score 136 for each patient profile may be generated, by processor 104, using regression analysis. Regression analysis may include any regression analysis technique including those disclosed in the present disclosure.

Still referring to FIG. 1, plurality of cohort labels 124 may be further characterized based on a plurality of clinical characteristics such as, without limitation, low-density lipoprotein cholesterol (LDL-C), lipoprotein (a), and/or the like. Additionally, or alternatively, condition score 136 may be calculated, by processor 104, based on plurality of clinical characteristics. In a non-limiting example, condition score 136 may include a 10-year atherosclerotic cardiovascular disease (ASCVD) risk score, wherein the 10-year ASCVD may be computed using a pooled cohort equation (PCE) at the time of ECG. In some cases, quantitative variables, such as high density lipoprotein level, total cholesterol level, and systolic blood pressure, and nearest datapoint to the ECG within 2 years prior to 1 year after an ECG may be used by processor 104 to calculate the 10-year ASCVD score. In some cases, for diagnosis data and smoking status, both structured and unstructured data may be leveraged during the calculation of the 10-year ASCVD score. In some cases, race/ethnicity information may be obtained directly from EHR/EMR as described above. In some cases, age at the time of ECG acquisition may also be used for such purpose. In other cases, treatment for hypertension may be identified by requiring a diagnosis for hypertension and the presence of a prescription of an antihypertensive on record. Further, other exemplary embodiments of plurality of cohort labels 124 may include, without limitation, lifestyle-based labels (e.g., Smoker", "Physically Active", "Vegan", and/or the like), genetic-based labels (e.g., BRCA1 Mutation", "ApoE4 Carrier," and/or the like), among others.

With continued reference to FIG. 1, in some cases, defining plurality of cohort labels 124 may further include identifying a plurality of sub-cohort labels 140 from plurality of patient profiles 112 based on a set of sub-cohort criteria 144. As used in this disclosure, "sub-cohort labels" are essentially further divisions within the main cohort groups that allow for more detailed and specific categorization of patients and/or patient profiles. In an embodiment, plurality of sub-cohort labels 140 may include secondary cohort labels that divides one or more cohort label within plurality of cohort labels 124 into smaller, more specific groups based on sub-cohort criteria 144. "Sub-cohort criteria," for the purpose of this disclosure, are specific factors or conditions that are used to define the sub-cohort labels. In some cases, sub-cohort criteria 144 may be selected based on a variety of factors, similar to pre-defined rules or criteria described herein used to define plurality of cohort labels 124; however, sub-cohort criteria 144 may be used to make more specific distinctions within a given cohort label e.g., at least a first cohort label 128 or at least a second cohort label 132.

Still referring to FIG. 1, in a non-limiting example, processor 104 may be configured to identify plurality of sub-cohort labels 140 from a given cohort label and/or sub-cohort label such as a group of patients with evidence of primary care at Mayo Clinic with residence in a state with Mayo primary care presence and evidence of primary care in the EHR/EMR within 2 years of or during the observation window, including one of the following: 1) appointments with primary care, family medicine, or general internal medicine; 2) clinical notes or ICD codes indicating a wellness or annual exam; and 3) evidence of primary care interventions, including vaccines on the Centers for Disease Control and Prevention adult immunization schedule or standard of care screening exams, within 2 years of or during the observation window. Processor 104 may be configured to identify a first sub-cohort label based on the given cohort label with a first set of sub-cohort criteria: aged 40-79 with sufficient clinical data available within 2 years before to 3 months after cohort entry to calculate ASCVD risk score using the PCE as described herein. One or more patient profiles may be excluded if they had ASCVD prior to cohort entry, including MI, peripheral arterial disease, stroke, PCI, CABG, or carotid artery intervention. Additionally, or alternatively, processor 104 may also be configured to identify a second sub-cohort label based on the given cohort label with a second set of sub-cohort criteria: aged 18-39 with a data availability requirement identical to first sub-cohort label and no ASCVD prior to cohort entry. Further, plurality of sub-cohort labels 140 may be identified from one or more cohort labels within plurality of cohort labels 124; for instance, and without limitation, plurality of sub-cohort labels 140 may be identified from patient profiles with at least one digital ECG waveform available as ECG data from data store 120, excluding other patient profiles used for other processing steps described below, such as, one or more training or validation data sets for machine learning models generation.

With continued reference to FIG. 1, in other embodiments, plurality of cohort labels 124 including at least a first cohort label 128 and at least a second cohort label 132, condition score 136, and/or plurality of sub-cohort labels 140 may be obtained, by processor 104, through an interpretation of ECG interpretation text as described above using a language processing module. using a language processing module. Language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to 1, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module may use a corpus of documents to generate associations between language elements in a language processing module, and diagnostic engine may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

With continued reference to FIG. 1, processor 104 is configured to assign plurality of cohort labels 124 to plurality of patient profiles 112. In some cases, plurality of cohort labels 124 may be assigned to plurality of patient profiles 112 using a label assignment algorithm, wherein the label assignment algorithm may be configured to map each cohort label of plurality of cohort labels 124 to plurality of patient profiles 112 based on the extracted data such as, without limitation, ECG interpretation text, condition score 136, and the like described herein. In some cases, implementation of label assignment algorithm may consider rules or criteria for each cohort label and/or each sub-cohort label and assign them to plurality of patient profiles 112 accordingly. In a non-limiting example, if a given cohort label is defined as "patients over 65 with a high cardiovascular risk score", label assignment algorithm may iterate plurality of patient profiles 112 to check each patient's age and cardiovascular risk score and assign the given cohort label to those who meet the criteria. Processor 104 may then apply rule or criteria set to the data in each patient profile of plurality of patient profiles 112. In a non-limiting example, one or more rule-based systems, decision trees, or more complex machine learning algorithms, among others, may be used by processor 104 to define a plurality of cohort labels 124 and/or plurality of sub-cohort labels. Assigning plurality of cohort labels 124 and/or plurality of sub-cohort labels may include assigning at least a first cohort label 128 such as, without limitation, cohort labels describing CAC, obstructive CAD, and regional left ventricular akinesis to a first set of patient profiles and assigning at least a second cohort label 132 to a second set of patient profiles, wherein the first set of patient profiles containing a plurality of disease cohorts and the second set of patient profiles containing a plurality of control cohorts corresponding to the plurality of disease cohorts.

With continued reference to FIG. 1, processor 104 may be configured to validate assignment of plurality of cohort labels 124. As used in this disclosure, "validation" is a process of ensuring that which is being "validated" complies with stakeholder expectations and/or desires. Stakeholders may include users, administrators, property owners, customers, and the like. Very often a specification prescribes certain testable conditions (e.g., metrics) that codify relevant stakeholder expectations and/or desires. In some cases, validation includes comparing a product, for example without limitation assignment of plurality of cohort labels, against a specification. In some cases, processor 104 may be additionally configured to validate a product by validating constituent sub-products. In some embodiments, processor 104 may be configured to validate any product or data, for example without limitation, assignment of plurality of cohort labels. In some cases, at least a machine-learning process, for example a machine-learning model, may be used to validate by processor 104. Computing device 104 may use any machine-learning process described in this disclosure for this or any other function. Additionally, or alternatively, plurality of cohort labels 124 and their assignment may be iteratively refined as processor 104 continues to receive new patient profiles; for instance, and without limitation, processor 104 may be configured to adjusted rules and/or criteria used to define plurality of cohort labels 124 and/or plurality of sub-cohort labels 140 and incorporate new information to improve accuracy of machine-learning model(s) generated by processor 104 based on such assignment as described in greater detail below.

With continued reference to FIG. 1, processor 104 is configured to generate condition training data 148 by correlating the plurality of patient profiles 112 with a plurality of condition identifiers 152. Condition training data 148 may include any training data as described herein. In one or more embodiments, one or more machine-learning models described herein may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from data store 120, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In a non-limiting example, training data such as condition training data 148 may be data sets that have already been converted from raw data whether manually, by machine, or any other method as described herein. Training data may include previous outputs such that one or more machine learning model iteratively produces outputs. Further, generating condition training data 148 may include matching second set of patient profiles (i.e., control cohort) to the first set of patient profiles (i.e., disease cohort) at a pre-defined ratio; for instance, and without limitation, patient profiles in control cohort may be matched 1:10 to disease cohort on age, sex, ECG acquisition year, and/or the like.

With continued reference to FIG. 1, as used in this disclosure, a plurality of "condition identifiers" refer to specific markers or indicators that help apparatus 100 in recognizing or diagnosing a particular medical condition or health status. In some cases, plurality of condition identifiers 152 may be based on a range of different data types or sources and serve to categorize or classify the health condition(s) associated with each patient profile. In another non-limiting example, plurality of condition identifiers 152 may include diagnostic codes, wherein the diagnostic codes are standardized codes used in healthcare to represent a particular diagnosis. International Classification of Diseases (ICD) codes, maintained by the World Health Organization, may serve as plurality of condition identifiers 152. For instance, and without limitation, condition identifier may include an ICD-10 code such as "I25.10". Such condition identifier may represent "Atherosclerotic heart disease of native coronary artery without angina pectoris". In some embodiments, plurality of condition identifiers 152 may include clinical measures, such as any clinical measurements described herein, for example and without limitation, condition score 136. In a non-limiting example, such condition identifiers may include a plurality of measurements taken during clinical assessments, such as blood pressure readings, cholesterol levels, body mass index (BMI), and the like. In an embodiment, a blood pressure reading above 140/90 mmHg may be a condition identifier for hypertension. Additionally, or alternatively, plurality of condition identifiers 152 may also include identifiers that describes symptoms or signs such as, without limitation, patient-reported symptoms (e.g., chest pain, shortness of breath) or signs observed by a healthcare provider (e.g., abnormal heart rhythm on an ECG as described above). In other embodiments, plurality of condition identifiers 152 may include genetic or molecular markers; for instance, and without limitation, the presence of the APOE4 allele could be a condition identifier for an increased risk of Alzheimer's disease. As an ordinary person skilled in the art, upon reviewing the entirety of this disclosure, may be aware of various condition identifiers may be used by apparatus 100 for generation of condition training data 148.

With continued reference to FIG. 1, generating condition training data 148 may include transforming plurality of patient profiles 112 and plurality of correlated condition identifier 152 into a format that can be used by machine learning model such as condition evaluation model as described below. In a non-limiting example, processor 104 may be configured to perform one or more data processing techniques such as one-hot encoding for categorical variables, normalization or standardization for numerical variables, or extraction of relevant features from image and/or text data. In some cases, correlation between plurality of patient profiles and plurality of condition identifiers may include either direct correlations (e.g., a specific symptom or diagnostic code) or indirect correlations (e.g., a combination of demographic factors, symptoms, and test results that collectively indicate a condition). In some cases, plurality of cohort labels 124 may be assigned to the condition training data 148 based on these correlations; for instance, and without limitation, one or more cohort labels may reflect the condition or outcome that machine learning model will be trained to predict (e.g., patients with identifiers for heart disease may be labeled as "heart disease patients," while those without would be labeled as "non-heart disease patients." Additionally, or alternatively, generating condition training data 148 may further include compilating labeled patient profiles into a training dataset. Such condition training data 148 may include feature vectors (representations of each patient profile) and their corresponding condition identifiers.

In one or more embodiments, and still referring to FIG. 1, generating condition training data 148 may include reconstructing a plurality of ECG image data as a function of ECG interpretation text described herein using contrastive learning. As used in this disclosure, "contrastive learning" is a type of unsupervised machine learning approach that learns to identify which examples are similar and which are not. In an embodiment, generating condition training data 148 may include paring a plurality of ECG images with their corresponding ECG interpretation texts. In some cases, ECG images and their corresponding ECG interpretation texts may be received from data store 120 as described above. In a non-limiting example, each pair may form a positive example (i.e., two items that are similar or connected in some ways). Processor 104 may utilize an artificial neural network (ANN) model, such as a convolutional neural network (CNN) as described below for plurality of ECG images and a natural language processing (NLP) model such as a transformer for the text, to extract plurality of features from both ECG image data and ECG interpretation texts. An ECG image reconstruction machine learning model may then be generated, by processor 104, using a plurality of ECG images and ECG interpretation texts pairs as training data. In some cases, ECG image reconstruction machine learning model may be configured to minimize the distance between the representations of a positive pair (ECG image and its corresponding text) in latent space and maximize the distance between the representations of a negative pair (ECG image and a non-corresponding text). In a non-limiting example, bidirectional loss may be implemented, by processor 104 to enable ECG image reconstruction machine learning model to encode relevant information in the embeddings, effectively capture the underlying structure of ECG image data and semantics of ECG interpretation texts, thereby allowing ECG image reconstruction machine learning model to generate discriminative representations that can be used for various downstream tasks such as, without limitation, classification, retrieval, or generation of ECG image data and/or ECG interpretation texts. Processor 104 may further use trained ECG image reconstruction machine learning model generate an ECG image that is close to the corresponding representation of ECG interpretation text for each patient profile of plurality of patient profiles or vice versa.

With continued reference to FIG. 1, in some cases, each condition identifier of plurality of condition identifiers 152 may include at least a condition risk factor identifier 156. A "condition risk factor identifier," for the purpose of this disclosure, is a specific marker or indicator associated with an increased likelihood of developing a particular health condition or disease. In some cases, at least a condition risk factor identifier may be based on known risk factors for various health conditions. In an embodiment, at least a condition risk factor identifier may include an identifier describing a non-modifiable risk factors (i.e., risk factors that cannot be changed or controlled by the individual); for instance, age, sex, ethnicity, family history, and/or the like are non-modifiable risk factors for many diseases. In a non-limiting example, having a family history of heart disease is a condition risk factor identifier for cardiovascular conditions. In another embodiment, at least a condition risk factor identifier may include a modifiable risk factors (i.e., risk factors that can be controlled, changed, or treated with interventions or lifestyle changes. Exemplary modifiable risk factors may include, without limitation, smoking, diet, physical activity levels, body mass index (BMI), blood pressure, cholesterol levels, and/or the like. In a non-limiting example, high cholesterol levels may be a condition risk factor identifier for cardiovascular conditions. Additionally, or alternatively, at least a condition risk factor identifier 156 may be generated by comparing first set of patient profiles (i.e., disease cohort) with second set of patient profiles (i.e., control cohort). In a non-limiting example, by comparing different set of patient profiles, processor 104 may recognize a patient's age may be a condition risk factor identifier for condition identifiers such as Alzheimer's disease or heart disease. A history of smoking may be a condition risk factor identifier for condition identifiers such as lung cancer or chronic obstructive pulmonary disease (COPD). A high BMI may be a condition risk factor identifier for condition identifier such as diabetes.

With continued reference to FIG. 1, at least a condition risk factor identifier 156 may be identified, by processor 104 using a classifier. In some cases, processor 104 may generate a condition risk factor classifier, wherein the condition risk factor classifier may be trained using condition training data described herein. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a processor 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, processor 104 may be configured to define additional sub-cohorts to understand the drivers of differences between (condition) risk classification described herein and calculated PCE-based risk. In a non-limiting example, processor 104 may compared clinical diagnoses and lab test results on record at the time of and up to 1 month after ECG assessment, using condition evaluation model as described below of plurality of cohort labels 124 described herein. Additional sub-cohorts may include, for example, and without limitation, a first additional sub-cohort defined as patients with low (<5%), borderline (5%≤risk<7.5%), or intermediate risk by PCE (7.5%≤risk<20%) that are classified as ASCVD positive by condition risk factor classifier described herein and a second additional sub-cohort defined as patients with intermediate (7.5%≤risk<20%) or high (≥20%) risk by PCE that are classified as ASCVD negative by condition risk factor classifier described herein. Additionally, or alternatively, processor 104 may identify data describing disease diagnoses available in plurality of patient profiles 112 for additional sub-cohorts and computed one or more statistical values such as, without limitation, a rate ratio and chi square statistic between the cohorts. Similarly, for patient profiles containing lab results with over 75% coverage of additional sub-cohorts, other statistical values such as, without limitation, a median and interquartile range for each lab test in each additional sub-cohort may be computed and the difference of the distribution of results between plurality of cohorts 124 using Cohen's D may be quantified. Further, for diagnoses, processor 104 may rank by the chi square statistic and report the top 15 results. In some cases, for lab test results, Cohen's D may be limited, by processor 104, to ≥0.15.

With continued reference to FIG. 1, processor 104 is configured to generate a condition evaluation model 160 using condition training data 148 and at least a machine-learning algorithm. As used in this disclosure, a "condition evaluation model" is an artificial intelligence (AI) or machine learning (ML) model that is trained to assess, classify, or predict a patient's health condition based on the information available in their patient profile. Generating condition evaluation model 160 may include training condition evaluation model 160 using condition training data 148 described herein, which includes plurality of patient profiles 112 and associated plurality of condition identifiers 152 each containing at least a condition risk factor identifier 156. In some cases, condition evaluation model 160 may incorporate other machine learning models such as, without limitation, condition score machine learning model, condition risk factor classifier, and/or the like. At least a machine-learning algorithm may include any machine-learning algorithms described herein. Additionally, or alternatively, processor 104 may be configured to validate trained condition evaluation model 160 using a separate set of data (i.e., validation data) to assess model performance. In a non-limiting example, model validation techniques such as accuracy, precision, recall, or area under the receiver operating characteristic curve (AUC-ROC) may be performed by processor 104, and condition evaluation model 160 may be adjusted or fine-tuned based on the results of one or more validation processes.

Still referring to FIG. 1, in some cases, condition evaluation model 160 may include a Time Series Convolutional Neural Network (TSCNN), wherein the TSCNN is a type of CNN that is designed to handle time series data. As used in this disclosure, a "convolutional neural network" is a type of artificial neural network used that uses convolution in place of general matrix multiplication in at least one layer. In an embodiment, CNN may include a plurality of layers, including convolutional layers, activation layers, pooling layers, and fully connected layers. Plurality of layers may work together to learn and extract features from the input data such as, without limitation, reconstructed ECG images described herein. In a non-limiting example, convolutional layer may apply a set of learnable filters (i.e., convolutional kernels) to image data through a sliding window operation, resulting in a set of feature maps. Each filter may be responsible for detecting a specific feature at different spatial locations in ECG image. CNN may include one or more activation layers, wherein the activation layers may introduce non-linearity into the network by applying an activation function, such as, without limitation, a Rectified Linear Unit (ReLU), to the output of convolutional layer. In some cases, such non-linearity may help CNN to learn and represent more complex relationships and patterns in ECG image. CNN may include one or more pooling layer configured to reduce the spatial dimensions of the feature maps by applying downsampling such as max-pooling or average pooling, to small, non-overlapping regions of the feature maps. Downsampling may reduce the computational complexity of the network, improve its generalization capabilities, and provides a form of translation invariance. CNN may include one or more fully Connected layers, wherein the fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, a reconstructed license plate region. Additionally, or alternatively, CNN may include a SoftMax Layer for potential classification tasks, wherein the SoftMax layer may be often added at the end of CNN to convert the output of the fully connected layer into one or more probability values for a plurality of categories. In some cases, SoftMax layer may include a SoftMax function configured to normalize the output such that the sum of the probabilities equals one.

Still referring to FIG. 1, TSCNN may leverage the spatial hierarchies that CNN described herein provide while also being designed to recognize temporal dependencies. In an embodiment TSCNN may accept time series data, wherein the time series data are data collected or recorded in a sequential manner over time. In a non-limiting example, each patient profile of plurality of patient profiles 112 may include data like heart rate, blood pressure, or ECG data that is collected continuously over a certain period of time. In another non-limiting example, each patient profile of plurality of patient profiles 112 may include a plurality of historical patient profiles as described above. In an embodiment, TSCNN may combine the strengths of CNNs with the temporal nature of time series data; for instance, and without limitation, time series data may be treated as a one-dimensional "image" by TSCNN, where the temporal dimension, in this case, is analogous to the spatial dimensions in an image. Additionally, or alternatively, TSCNNs may apply one or more convolutional layers to plurality of patient profiles 112 to extract and learn important temporal features. For example, and without limitation, TSCNN may learn to recognize certain patterns in the ECG data (like the P wave, QRS complex, or T wave) that are indicative of specific heart conditions. One key advantage of TSCNN is its ability to handle large amounts of time series data efficiently. In some cases, TSCNN may process plurality of patient profiles 112 in a parallelized way, which can be much faster than traditional time series models such as autoregressive integrated moving average (ARIMA) models or recurrent neural networks (RNNs).

With continued reference to FIG. 1, processor 104 is configured to determine a patient survival profile 164 for a user-inputted patient profile 168 using condition evaluation model 160. As used in this disclosure, a "patient survival profile" is a predictive model or estimation of a patient's probability of survival over a specified timeframe, based on a combination of their demographic, clinical, genetic data, and any other data within the corresponding patient profile. In some cases, patient survival profile may be generated as a function of condition identifier 152 (including at least a condition risk factor identifier 156) as described herein. A "user-inputted patient profile," for the purpose of this disclosure, refers to specific data or information about a patient that is manually entered into system by a user. In some cases, user may include, without limitation, healthcare provider, data entry specialist, patient, and/or the like. In a non-limiting example, user-inputted patient profile 168 may include one or more new/unseen patient profiles within plurality of patient profiles 112 (e.g., patient profile in test dataset). In another non-limiting example, user-inputted patient profile 168 may include a plurality of electrocardiogram (ECG) signals from a user. In such embodiments, user-inputted patient profile 168 containing ECG signals may be received through one or more sensor (e.g., standard 12-lead ECG). Condition evaluation model 160 may be configured to predict one or more data elements e.g., likelihood of surviving of a given disease or condition based on current health status. Additionally, or alternatively, patient survival profile 164 may include a patient's likelihood of survival. In some cases, patient survival profile 164 may be assessed using a survival analysis, wherein the survival analysis may be a branch of statics that deals with time time-to-event data, and wherein the events may include, without limitation, death, disease progression, recurrence, and/or the like. In a non-limiting example, processor 104 may implement one or more techniques and/or algorithms such as Cox proportional hazards model or Kaplan-Meier survival curves that may be used to estimate the patient's probability of survival over time based on their patient profiles. Further, patient survival profile 164 may be used for risk stratification. In a non-limiting example, patients may be divided into different risk groups based on their predicted survival.

In a non-limiting example, patient survival profile 164 may include a cancer survival profile. In some cases, user-inputted patient profile may include various factors such as, without limitation, type and stage of cancer, patient's performance status, genetic characteristics of the tumor, treatments the patient has received, and/or the like. Patient survival profile output by condition evaluation model 160 based on such user-inputted patient profile may include an estimation of patient's likelihood of surviving for a certain number of years, or their risk of recurrence. In another non-limiting example, patient survival profile 164 may include a cardiovascular survival profile. In some cases, user-inputted patient profile may include various factors such as, without limitation, patient's age, sex, cholesterol levels, blood pressure, smoking status, history of heart disease, historical ECG data, and/or the like. Patient survival profile output by condition evaluation model 160 based on such user-inputted patient profile may include an estimation of the patient's risk of experiencing a heart attack or stroke within the next 10 years. In a further non-limiting example, survival profile 164 may include a COVID-19 survival profile. In some cases, user-inputted patient profile may include various factors such as patient's age, sex, comorbidities (like diabetes or lung disease), severity of COVID-19 symptoms, and/or the like. Patient survival profile output by condition evaluation model 160 based on such user-inputted patient profile may include a prediction of the patient's likelihood of surviving the disease or their risk of needing intensive care.

With continued reference to FIG. 1, relationship between outputs of condition evaluation model 160 including outputs of other machine learning models described herein and known clinical risk factors for ASCVD may be examined by processor 104. In an embodiment, such examination may include one or more evaluation of quantitative measure such as, without limitation, LDL-C, Lp(a), and the PCE score, across a broad data population by identifying all ECGs within ECG data 116 with paired condition risk factor identifiers within −2 years to +1 year of ECG acquisition. In some cases, only a first ECG-risk factor pair may be used for analysis and generation of condition training data 148 or validation datasets for condition evaluation model 160 were excluded from the analysis. Across all machine learning models described herein, in positive versus negative condition identifier or condition risk factor identifier, LDL-C may be slightly lower, Lp(a) may also be slightly higher, and PCE-score may be considerably higher as well. In some cases, a Mann-Whitney U test may be performed, by processor 104, to assess for differences in LDL-C, Lp(a), and a PCE score in plurality of patient profiles that tested positive versus negative on a given machine learning model. All results were significant with $p<10^{-15}$.

Still referring to FIG. 1, generated patient survival profile 164 may be displayed using a visual interface 172. In a non-limiting example, processor 104 is configured to display patient survival profile 164 at a display device (i.e., a hardware component that presents information visually to a user), wherein the display device may include visual interface 172. A "visual interface," as used in this disclosure, is a graphical user interface (GUI) that conveys information and facilitates interaction between users and apparatus 100. In an embodiment, visual interface 172 may display plurality of patient profiles 112, condition score 140, condition identifier 152 and/or condition risk factor identifier 156, patient survival profile 164, and any data described herein, and permit user (e.g., healthcare providers, doctors, patients, and/or the like) to manipulate, edit, or otherwise interact with displayed. In an embodiment, visual interface 172 may include a window in which patient survival profile 164 may be displayed. In some cases, visual interface 172 may include one or more graphical locator and/or cursor facilities allowing one or more users to interact with patient survival profile 164; for instance, and without limitation, using a touchscreen, touchpad, mouse, keyboard, and/or other manual data entry device. In some cases, visual interface 172 may include one or more menus and/or panels permitting selection of measurements, models, visualization of data to be displayed and/or used, elements of data, functions, or other aspects of patient survival profile 164 to be edited, added, and/or manipulated, options for importation of and/or linking to application programmer interfaces (APIs), exterior services, data source, machine-learning models, and/or algorithms, or the like. Persons skilled in the art, upon reviewing the entirety of this disclosure, will be aware of various ways in which visual interface 172 and/or elements thereof may be implemented and/or used as described in this disclosure.

In one or more embodiments, and still referring to FIG. 1, visual interface 172 may include one or more user input fields. For example, and without limitation, As used in this disclosure, an "user input field" is a graphical or interactive element in GUI that allows user to input or enter data. In some cases, user input fields may be configured to receive user-inputted patient profile 168 described herein. In a non-limiting example, user input fields may include, without limitation, a text box, a dropdown menu, a checkbox, a radio button, and/or any other interactive components that allows entities to provide any data described herein. In some cases, user input field may include an event handler that responds to user interactions, wherein the "event handler," for the purpose of this disclosure, is a piece of computer program or software function that is associated with a specific event. In some cases, event handler may generate prompts for further information, may compare data to validation rules such as requirements that the data in question be entered within certain numerical ranges, and/or may modify data and/or generate warnings to entities in response to such requirements. Further, event handler may convert data into expected and/or desired formats, for instance such as date formats, image format, document format, name formats, and/or the like.

Figure 2:
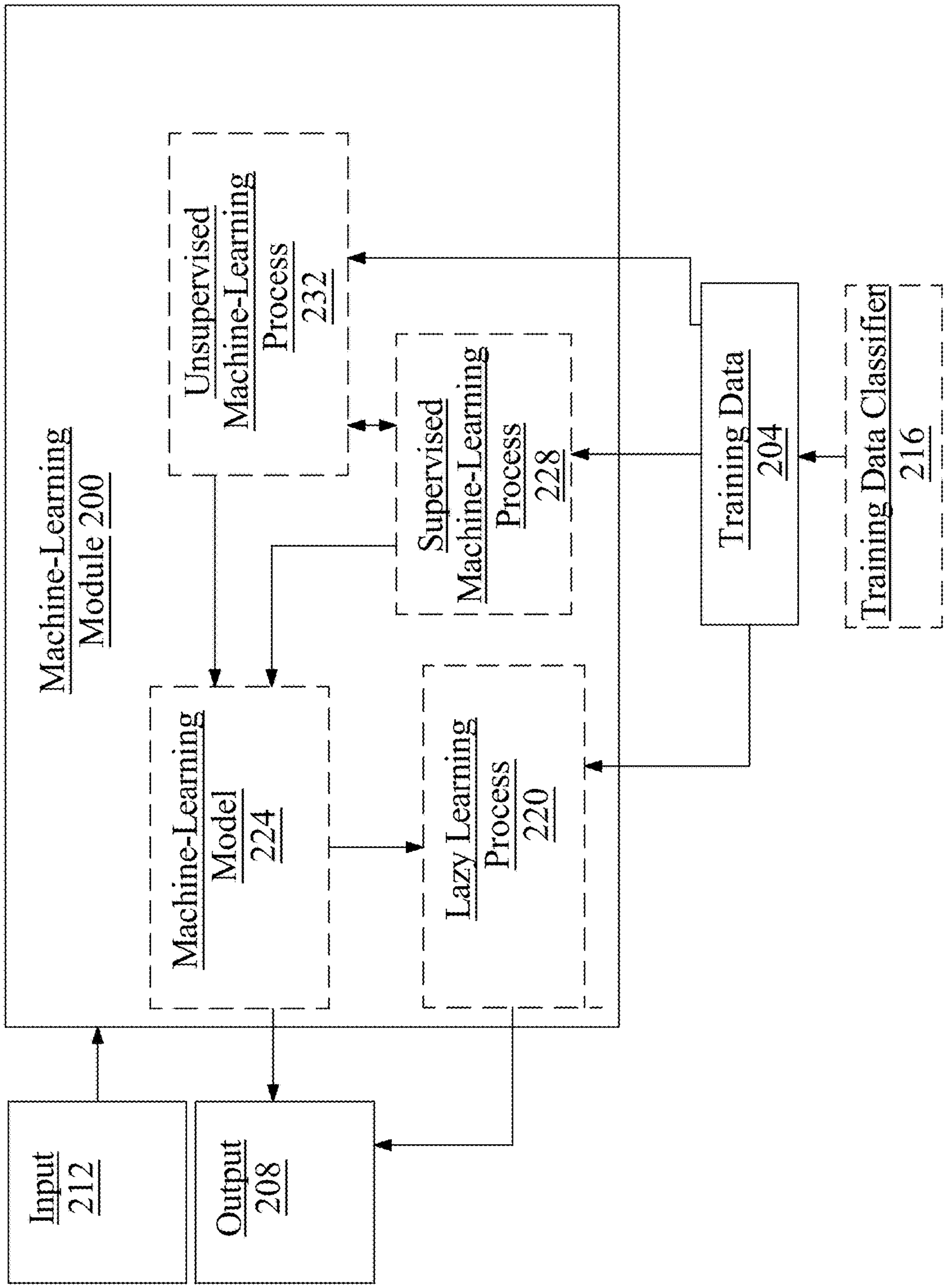
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, training data 204 may include condition training data containing a plurality of patient profiles as input correlated to a plurality of condition identifiers as output as described above with reference to FIG. 1.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to a plurality of cohort labels, sub-cohort labels, condition identifiers, condition risk factor identifiers, and/or the like as described above with reference to FIG. 1.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include plurality of patient profiles as described above as inputs, condition identifiers and/or patient survival profile as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 232. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 232 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 232 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 232 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
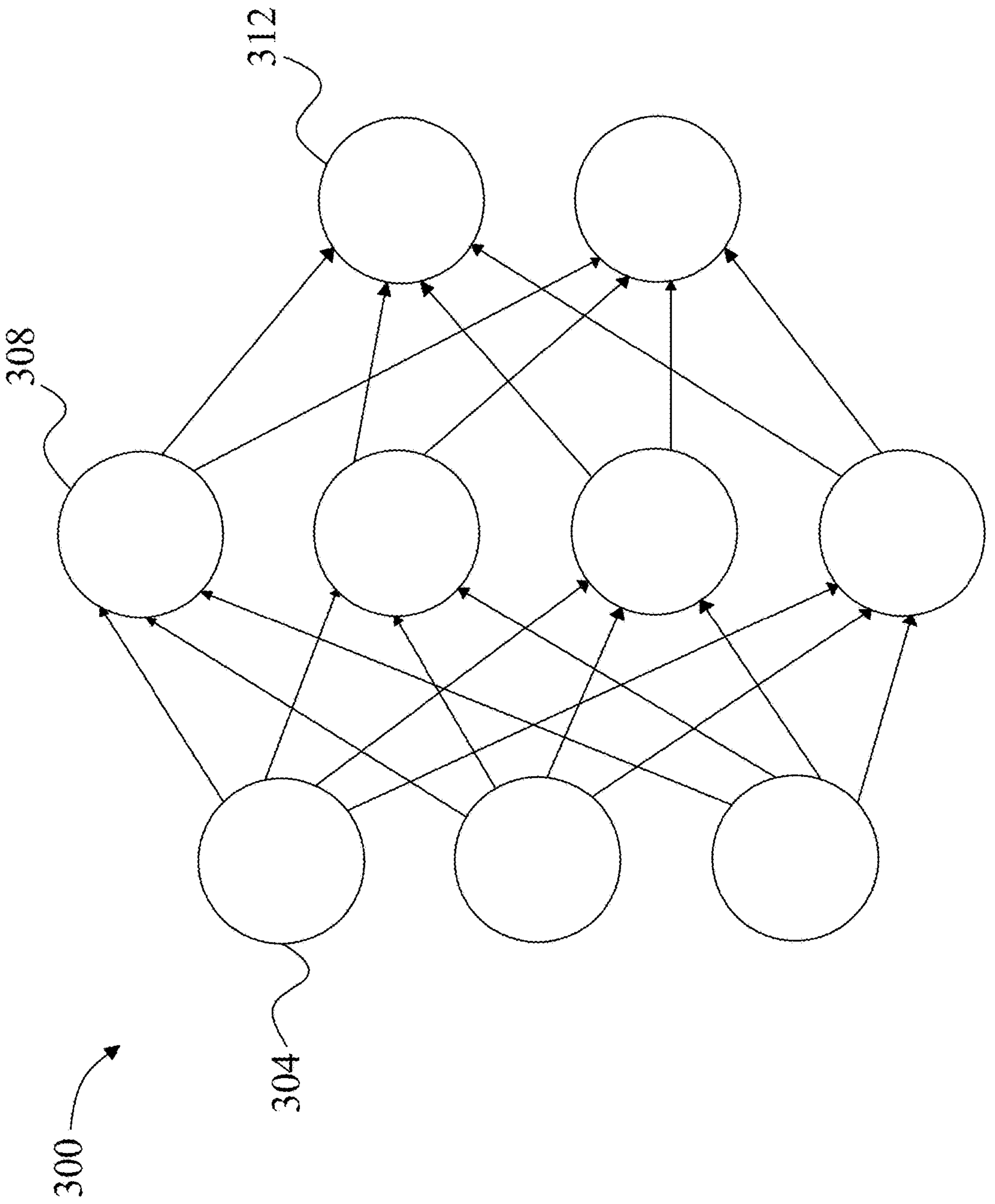
FIG. 3 is a diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
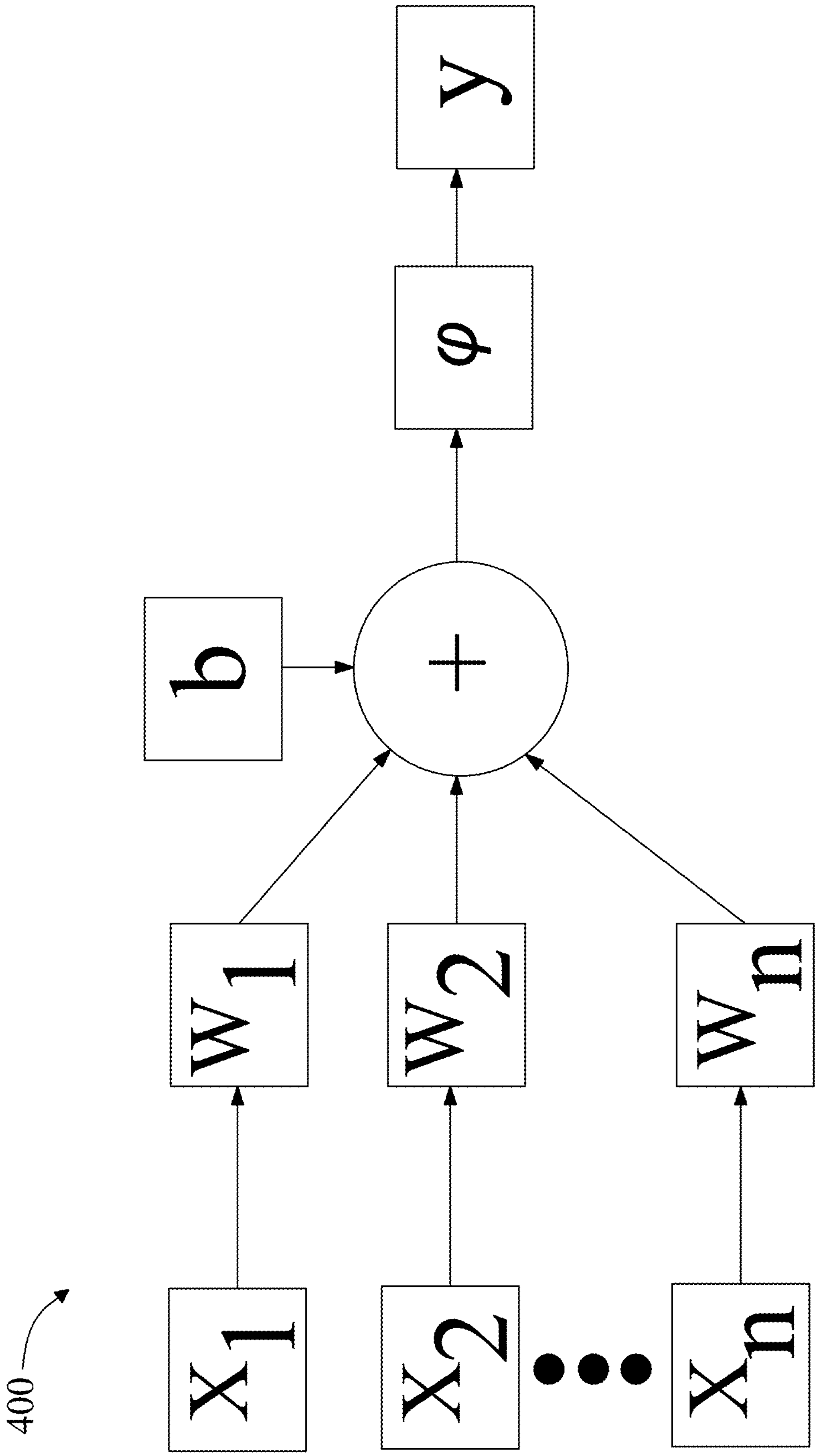
FIG. 4 is a diagram of an exemplary embodiment of a node of a neural network.

Referring now to FIG. 4, an exemplary embodiment of a node 400 of a neural network is illustrated. A node may include, without limitation, a plurality of inputs x/that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as f(x)=max (0, x), a "leaky" and/or "parametric" rectified linear unit function such as f(x)=max (ax, x) for some α, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\Sigma_i x_i}$$

where the inputs to an instant layer are $x_i$, a swish function such as f(x)=x*sigmoid (x), a Gaussian error linear unit function such as $f(x)=\alpha(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
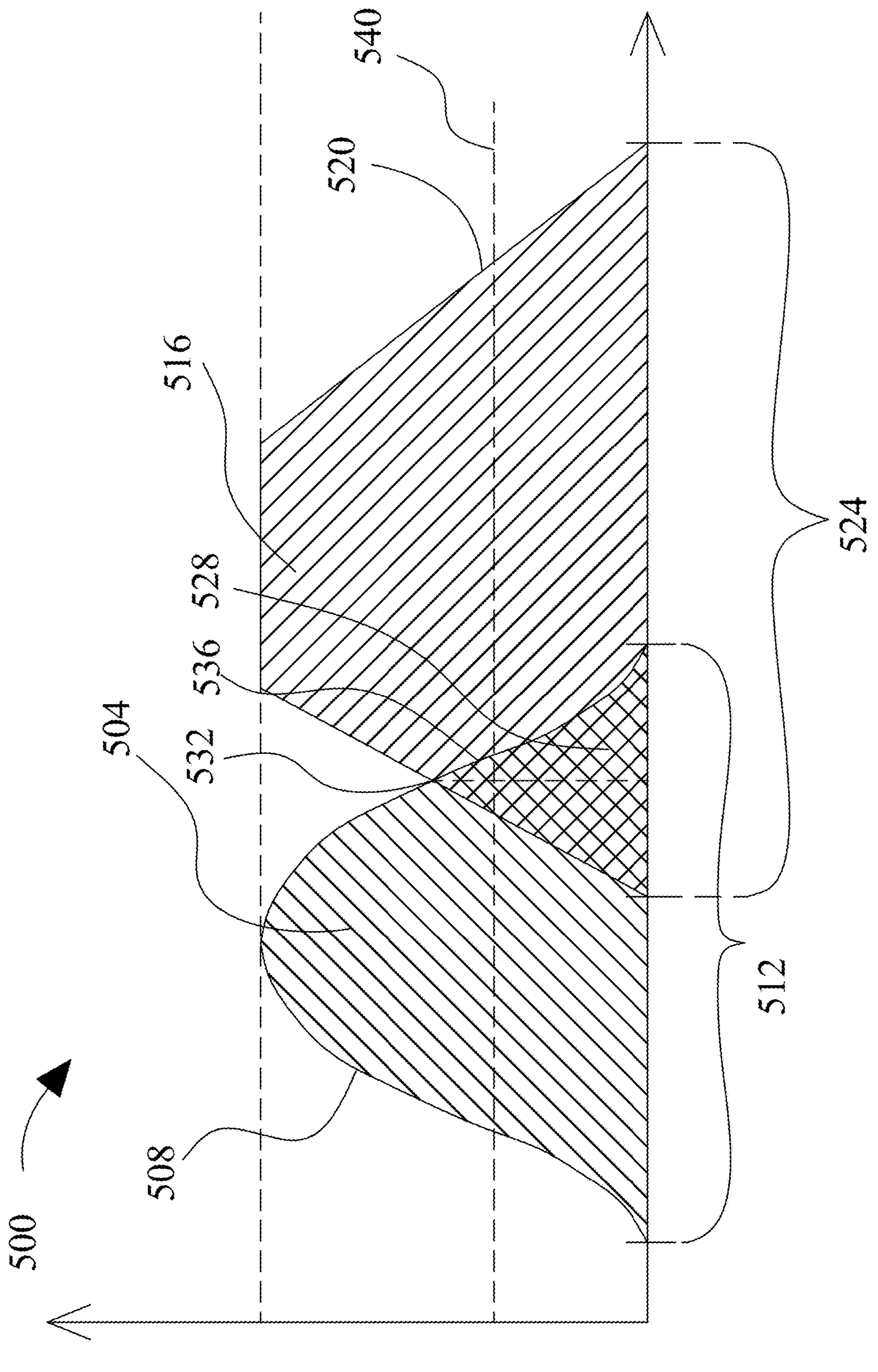
FIG. 5 is an illustration of an exemplary embodiment of fuzzy set comparison.

Referring now to FIG. 5, an exemplary embodiment of fuzzy set comparison 500 is illustrated. A first fuzzy set 504 may be represented, without limitation, according to a first membership function 508 representing a probability that an input falling on a first range of values 512 is a member of the first fuzzy set 504, where the first membership function 508 has values on a range of probabilities such as without limitation the interval [0,1], and an area beneath the first membership function 508 may represent a set of values within first fuzzy set 504. Although first range of values 512 is illustrated for clarity in this exemplary depiction as a range on a single number line or axis, first range of values 512 may be defined on two or more dimensions, representing, for instance, a Cartesian product between a plurality of ranges, curves, axes, spaces, dimensions, or the like. First membership function 508 may include any suitable function mapping first range 512 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 5, first fuzzy set 504 may represent any value or combination of values as described above, including output from one or more machine-learning models. A second fuzzy set 516, which may represent any value which may be represented by first fuzzy set 504, may be defined by a second membership function 520 on a second range 524; second range 524 may be identical and/or overlap with first range 512 and/or may be combined with first range via Cartesian product or the like to generate a mapping permitting evaluation overlap of first fuzzy set 504 and second fuzzy set 516. Where first fuzzy set 504 and second fuzzy set 516 have a region 528 that overlaps, first membership function 508 and second membership function 520 may intersect at a point 532 representing a probability, as defined on probability interval, of a match between first fuzzy set 504 and second fuzzy set 516. Alternatively, or additionally, a single value of first and/or second fuzzy set may be located at a locus 536 on first range 512 and/or second range 524, where a probability of membership may be taken by evaluation of first membership function 508 and/or second membership function 520 at that range point. A probability at 528 and/or 532 may be compared to a threshold 540 to determine whether a positive match is indicated. Threshold 540 may, in a non-limiting example, represent a degree of match between first fuzzy set 504 and second fuzzy set 516, and/or single values therein with each other or with either set, which is sufficient for purposes of the matching process; for instance, threshold may indicate a sufficient degree of overlap between an output from one or more machine-learning models. Alternatively, or additionally, each threshold may be tuned by a machine-learning and/or statistical process, for instance and without limitation as described in further detail below.

Figure 6:
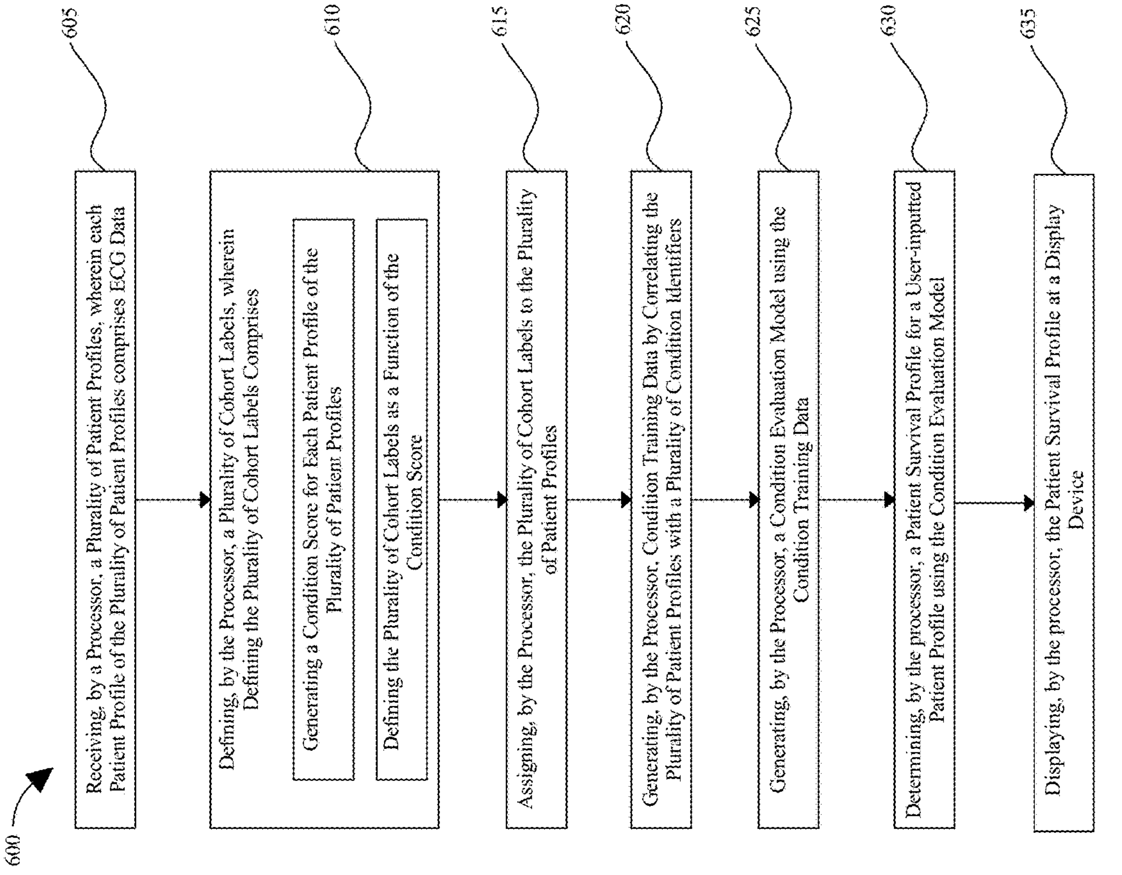
FIG. 6 is a flow diagram of an exemplary method for determining a patient survival profile using artificial intelligence-enabled electrocardiogram (ECG)

Now referring to FIG. 6, a flow diagram of an exemplary embodiment of a method 600 for determining a patient survival profile using artificial intelligence-enabled electrocardiogram (ECG) is illustrated. The method 600 includes a step 605 of receiving, by a processor, a plurality of patient profiles, wherein each patient profile of the plurality of patient profiles includes ECG data. In some embodiments, the ECG data may include an ECG interpretation text. This may be implemented, without limitation, as described above with reference to FIGS. 1-5.

With continued reference to FIG. 6, method 600 includes a step 610 of defining, by the processor, a plurality of cohort labels, wherein defining the plurality of cohort labels includes generating a condition score for each patient profile of the plurality of patient profiles and defining the plurality of cohort labels as a function of the condition score. In some embodiments, generating the condition score may include extracting the condition score from the plurality of patient profiles using a plurality of regular expressions, wherein the plurality of patient profiles further includes a plurality of electronic health records (EHRs). In some embodiments, defining the plurality of cohort labels further includes identifying a plurality of sub-cohort labels from the plurality of patient profiles based on a set of sub-cohort criteria. This may be implemented, without limitation, as described above with reference to FIGS. 1-5.

With continued reference to FIG. 6, method 600 includes a step 615 of assigning, by the processor, the plurality of cohort labels to the plurality of patient profiles. In some embodiments, the plurality of cohort labels may include at least a first cohort label and at least a second cohort label associated with the at least a first cohort label. In some embodiments, assigning the plurality of cohort labels may include assigning the at least a first cohort label to a first set of patient profiles and assigning the at least a second cohort label to a second set of patient profiles, wherein the first set of patient profiles is a disease cohort, and the second set of patient profiles is a control cohort. This may be implemented, without limitation, as described above with reference to FIGS. 1-5.

With continued reference to FIG. 6 method 600 includes a step 620 of generating, by the processor, condition training data by correlating the plurality of patient profiles with a plurality of condition identifiers. In some embodiments, generating the condition training data may include matching the second set of patient profiles to the first set of patient profiles at a pre-defined ratio. In some embodiments, each condition identifier of the plurality of condition identifiers may include at least a condition risk factor identifier generated by comparing the first set of patient profiles with the second set of patient profiles. This may be implemented, without limitation, as described above with reference to FIGS. 1-5.

With continued reference to FIG. 6, method 600 includes a step 625 of generating, by the processor, a condition evaluation model using the condition training data. In some embodiments, the condition evaluation model may include a time series convolution neural network (TSCNN). In some embodiments, generating the condition evaluation model may include generating a condition risk factor classifier for each condition identifier of the plurality of condition identifiers using the condition training data. This may be implemented, without limitation, as described above with reference to FIGS. 1-5.

With continued reference to FIG. 6, method 600 includes a step 630 of determining, by the processor, a patient survival profile for a user-inputted patient profile using the condition evaluation model. This may be implemented, without limitation, as described above with reference to FIGS. 1-5.

With continued reference to FIG. 6, method 600 includes a step 635 of displaying, by the processor, a patient survival profile at a display device. In some embodiments, display device may include a visual interface. This may be implemented, without limitation, as described above with reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
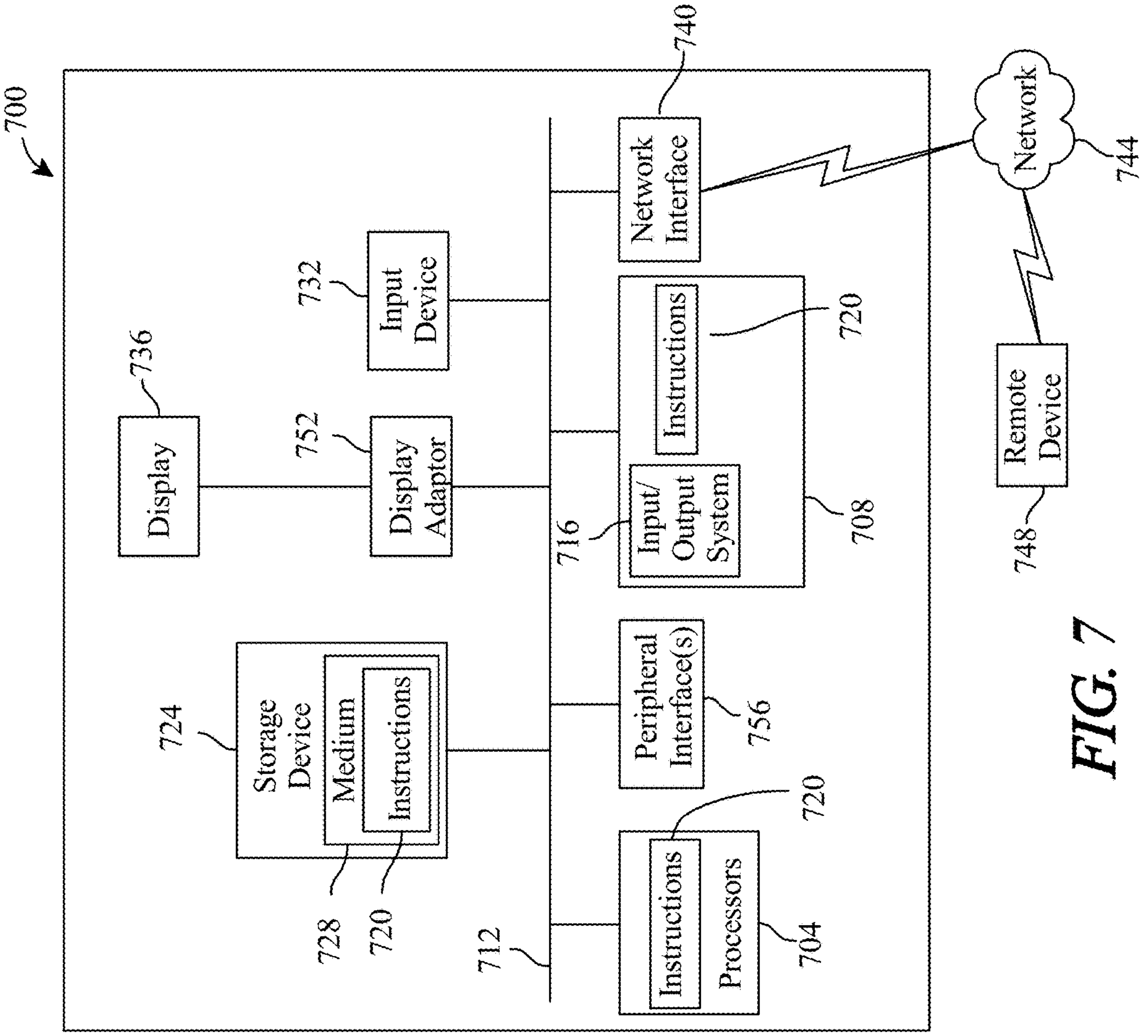
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1294 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for determining a patient survival profile using artificial intelligence-enabled electrocardiogram (ECG), the apparatus comprising:
- at least a processor; and
- a memory communicatively connected to the at least a processor, wherein the memory contains instructions configuring the at least a processor to:
  - receive a plurality of patient profiles, wherein each patient profile of the plurality of patient profiles comprises ECG data, wherein the ECG data comprises time-series electrical signal data acquired from a plurality of electrodes;
  - define a plurality of cohort labels, wherein the plurality of cohort labels comprises at least a first cohort label corresponding to a first set of patient profiles and at least a second cohort label associated with the at least a first cohort label corresponding to a second set of patient profiles and wherein defining the plurality of cohort labels comprises:
    - receiving condition score training data from a data store, wherein the condition score training data comprises the plurality of patient profiles as input correlated to a plurality of condition scores as output;
    - training a condition score machine-learning model using the condition score training data;
    - generating a condition score for each patient profile of the plurality of patient profiles as a function of the trained condition score machine-learning model; and
    - defining the plurality of cohort labels as a function of the condition score generated using the trained condition score machine-learning model;
  - assign the plurality of cohort labels to the plurality of patient profiles;
  - generate condition training data by correlating the plurality of patient profiles comprising the ECG data with a plurality of condition identifiers comprising preconditioning the condition training data by preconditioning at least an image of the plurality of patient profiles and upsampling the at least an image corresponding to the plurality of patient profiles to a number of pixels and interpolating added pixels into the upsampled at least an image, wherein generating the condition training data further comprises reconstructing ECG image data from ECG interpretation text using a contrastive learning model by encoding ECG signal features and corresponding textual features into a shared latent space;
- generate a condition evaluation model using the condition training data and at least one machine-learning algorithm further comprising:
  - receiving the condition training data, wherein the condition training data correlates the plurality of patient profiles to an associated plurality of condition identifiers, wherein the associated plurality of condition identifiers comprise clinical measurements associated with the condition score generated using the trained condition score machine-learning model, wherein each condition identifier comprises at least a condition risk factor identifier;
  - training, iteratively, the condition evaluation model using the condition training data, wherein training the condition evaluation model includes retraining the condition evaluation model with feedback from previous iterations of the condition evaluation model;
- determine, by the condition evaluation model, a user patient survival profile, output in response to a user patient profile including user ECG data inputted to the condition evaluation model; and
- display the patient survival profile at a visual interface, wherein the visual interface comprises a graphical user interface on a display device and the patient survival profile is displayed in a window on the graphical user interface that is accessed by a user from a menu on the graphical user interface, wherein the visual interface is configured to permit the user to interact with the displayed patient profile and launch a linkage to an exterior service for data exchange.

2. The apparatus of claim 1, wherein the ECG data comprises an ECG interpretation text.

3. The apparatus of claim 1, wherein generating the condition score comprises:
- extracting the condition score from the plurality of patient profiles using a plurality of regular expressions, wherein the plurality of patient profiles further comprises a plurality of electronic health records (EHRs).

4. The apparatus of claim 1, wherein:
- the first set of patient profiles is a disease cohort; and
- the second set of patient profiles is a control cohort.

5. The apparatus of claim 1, wherein defining the plurality of cohort labels further comprises:

identifying a plurality of sub-cohort labels from the plurality of patient profiles based on a set of sub-cohort criteria.

6. The apparatus of claim 1, wherein the condition evaluation model comprises a time series convolution neural network (TSCNN).

7. The apparatus of claim 1, wherein each condition identifier of the plurality of condition identifiers comprises:

at least a condition risk factor identifier generated by comparing the first set of patient profiles with the second set of patient profiles.

8. The apparatus of claim 1, wherein generating the condition evaluation model comprises:

generating a condition risk factor classifier for each condition identifier of the plurality of condition identifiers using the condition training data.

9. A method for determining a patient survival profile using artificial intelligence-enabled electrocardiogram (ECG), the method comprising:

receiving, by a processor, a plurality of patient profiles, wherein each patient profile of the plurality of patient profiles comprises ECG data, wherein the ECG data comprises time-series electrical signal data acquired from a plurality of electrodes;

defining, by the processor, a plurality of cohort labels, wherein the plurality of cohort labels comprises at least a first cohort label corresponding to a first set of patient profiles and at least a second cohort label associated with the at least a first cohort label corresponding to a second set of patient profiles and wherein defining the plurality of cohort labels comprises:

receiving condition score training data from a data store, wherein the condition score training data comprises the plurality of patient profiles as input correlated to a plurality of condition scores as output;

training a condition score machine-learning model using the condition score training data;

generating a condition score for each patient profile of the plurality of patient profiles as a function of the trained condition score machine-learning model; and defining the plurality of cohort labels as a function of the condition score generated using the trained condition score machine-learning model;

assigning, by the processor, the plurality of cohort labels to the plurality of patient profiles;

generating, by the processor, condition training data by correlating the plurality of patient profiles comprising the ECG data with a plurality of condition identifiers comprising preconditioning the condition training data by preconditioning at least an image of the plurality of patient profiles and upsampling the at least an image corresponding to the plurality of patient profiles to a number of pixels and interpolating added pixels into the upsampled at least an image, wherein generating the condition training data further comprises reconstructing ECG image data from ECG interpretation text using a contrastive learning model by encoding ECG signal features and corresponding textual features into a shared latent space;

generating, by the processor, a condition evaluation model using the condition training data and at least one machine-learning algorithm further comprising:

receiving the condition training data, wherein the condition training data correlates the plurality of patient profiles to an associated plurality of condition identifiers, wherein the associated plurality of condition identifiers comprise clinical measurements associated with the condition score generated using the trained condition score machine-learning model, wherein each condition identifier comprises at least a condition risk factor identifier;

training, iteratively, the condition evaluation model using the condition training data, wherein training the condition evaluation model includes retraining the condition evaluation model with feedback from previous iterations of the condition evaluation model;

determining, by the condition evaluation model, a user patient survival profile, output in response to a user patient profile including user ECG data inputted to the condition evaluation model; and displaying, by the processor, the patient survival profile at a visual interface, wherein the visual interface comprises a graphical user interface on a display device and the patient survival profile is displayed in a window on the graphical user interface that is accessed by a user from a menu on the graphical user interface, wherein the visual interface is configured to permit the user to interact with the displayed patient profile and launch a linkage to an exterior service for data exchange.

10. The method of claim 9, wherein the ECG data comprises an ECG interpretation text.

11. The method of claim 9, wherein generating the condition score comprises:

extracting the condition score from the plurality of patient profiles using a plurality of regular expressions, wherein the plurality of patient profiles further comprises a plurality of electronic health records (EHRs).

12. The method of claim 9, wherein:

the first set of patient profiles is a disease cohort; and the second set of patient profiles is a control cohort.

13. The method of claim 9, wherein defining the plurality of cohort labels further comprises:

identifying a plurality of sub-cohort labels from the plurality of patient profiles based on a set of sub-cohort criteria.

14. The method of claim 9, wherein the condition evaluation model comprises a time series convolution neural network (TSCNN).

15. The method of claim 9, wherein each condition identifier of the plurality of condition identifiers comprises:

at least a condition risk factor identifier generated by comparing the first set of patient profiles with the second set of patient profiles.

16. The method of claim 9, wherein generating the condition evaluation model comprises:

generating a condition risk factor classifier for each condition identifier of the plurality of condition identifiers using the condition training data.

* * * * *